United States Patent [19]

Goodenough

[11] 4,068,127

[45] Jan. 10, 1978

[54] X-RAY GENERATING APPARATUS COMPRISING MEANS FOR ROTATING THE FILAMENT

[75] Inventor: David J. Goodenough, Buckeystown, Md.

[73] Assignee: The United States of America as represented by the Department of Health, Education and Welfare, Washington, D.C.

[21] Appl. No.: 703,378

[22] Filed: July 8, 1976

[51] Int. Cl.[2] .......................... A61B 6/00; H05G 1/00; H05G 1/70

[52] U.S. Cl. .................................... 250/402; 250/406; 313/60

[58] Field of Search .................... 250/406, 402; 313/60

[56] References Cited

U.S. PATENT DOCUMENTS 2,493,606 1/1950 Waterton ............................ 250/406

*Primary Examiner*—Alfred E. Smith

*Assistant Examiner*—T. N. Grigsby

*Attorney, Agent, or Firm*—Browdy and Neimark

[57] ABSTRACT

An X-ray apparatus provides rotationally symmetric, Gaussian-like focal spot distributions. The apparatus may be constituted by an X-ray tube having a glass envelope, a cathode in the form of a filament for providing thermionically emitted electrons and an anode. The anode is of conical shape and can be rotated. The cathode is arranged to be rotated about an axis perpendicular to the plane of the filament and passing through its central point. The apparatus may be constituted by a conventional X-ray tube which is rotatable about an axis coaxial with the central ray of the X-ray field which emerges from the tube. The apparatus may be constituted by a conventional X-ray tube, which is stationary, in combination with a mechanism which effects rotation of the X-ray image receptor and the object being to be examined about an axis coaxial with the central ray of the X-ray field.

19 Claims, 2 Drawing Figures

X-RAY GENERATING APPARATUS COMPRISING MEANS FOR ROTATING THE FILAMENT

FIELD OF THE INVENTION

This invention relates to X-ray apparatus which produce improved radiographic images. The present invention relates, more particularly, to X-ray apparatus which have rotationally symmetric, Gaussian-like focal spot X-ray intensity distributions which can produce superior radiographic images in certain situations. The apparatus may be constructed as an X-ray tube.

BACKGROUND OF THE INVENTION

Conventional X-ray tubes commonly use rotation of the anode to dissipate heat. Such rotation is distinctly different from rotation of the cathode about its central point which will affect the X-ray intensity distribution of the X-ray tube focal spot, as found at the radiographic image receptor.

A typical X-ray tube is characterized by a focal spot which has a non-uniform, double peaked intensity distribution. This type of distribution may result in either a double image or a sharp false image, and is often the limiting factor to the diagnostic usefulness of certain radiographic magnification procedures involving objects of subfocal dimensions. Focal spots with a Gaussian-like intensity distribution have been advocated not only because of the need for increased high frequency information, but also, because of the need for elimination of spurious resolution.

Electron beam focusing techniques have been used in conventional X-ray tubes to produce small focal spots with Gaussian-like intensity distributions. Radiographs have been shown which illustrate the diagnostic effect of such focal spots in small vessel angiography. It has been pointed out, however, that in the case of microfocal spots obtained with focusing voltage techniques, the focal spot size depends not only upon the focusing voltage, but also upon the tube voltage. The required type of intensity distribution can be maintained only with a restricted set of tube voltages.

It has been theorized that the non-uniform double peaked intensity distribution results from the difference in pathways that electrons coming from the back and sides of the cathode filament follow in reaching the anode. These differences in pathways create a non-uniform distribution of electrons impinging on the anode and thus, ultimately create the non-uniform focal spot distribution of X-rays.

The required type of intensity distribution can be maintained, in these known conventional arrangements, only with a restricted set of tube and focusing voltages. Thus, the operational flexibility of X-ray appratus using such tubes has been limited. These shortcomings are distinct disadvantages.

SUMMARY OF THE INVENTION

It is the principal object of the present invention to provide an X-ray apparatus which provides rotationally symmetric, Gaussian-like focal spot distributions which do not depend on a restricted set of tube voltages and avoids the disadvantages noted above.

It is another object of the present invention to provide an X-ray apparatus which provides a focal spot which is not characterized by a non-uniform, double peaked intensity distribution.

It is a further object of the present invention to provide an X-ray apparatus which avoids the production of double images during operation.

It is an additional object of the present invention to provide an X-ray apparatus which avoids the production of sharp false images during operation.

It is still another object of the present invention to provide an X-ray apparatus which achieves symmetric focal spots of Gaussian-like intensity distributions, without using special focusing techniques.

It is still another object of the present invention to provide an X-ray apparatus which in use can produce images which have substantially uniform definition in all radial directions.

The foregoing objects, as well as others which are to become clear from the text below, are achieved in accordance with the present invention by providing an X-ray apparatus having an anode, a cathode and means for providing a rotationally symmetric, Gaussian-like focal spot distribution. The apparatus may be desirably housed within an envelope and thus take the form of an X-ray tube.

An X-ray apparatus according to an exemplary embodiment of the present invention is provided with a cathode in the form of a filament which has a central point and lies in a given plane. Means are provided for rotating the filament about an axis which passes through the central point and is perpendicular to the given plane.

In a possible embodiment, a conventional X-ray tube can be arranged to rotate about an axis coaxial with the central ray of the X-ray field which emerges from the tube.

In an additional possible embodiment, a conventional X-ray tube, which is stationary, is combined with a mechanism which effects rotation of the X-ray image receptor and the object to be examined about an axis coaxial with the central ray of the X-ray field.

DETAILED DESCRIPTION OF THE PREFERRED EMBODIMENTS

Figure 1:
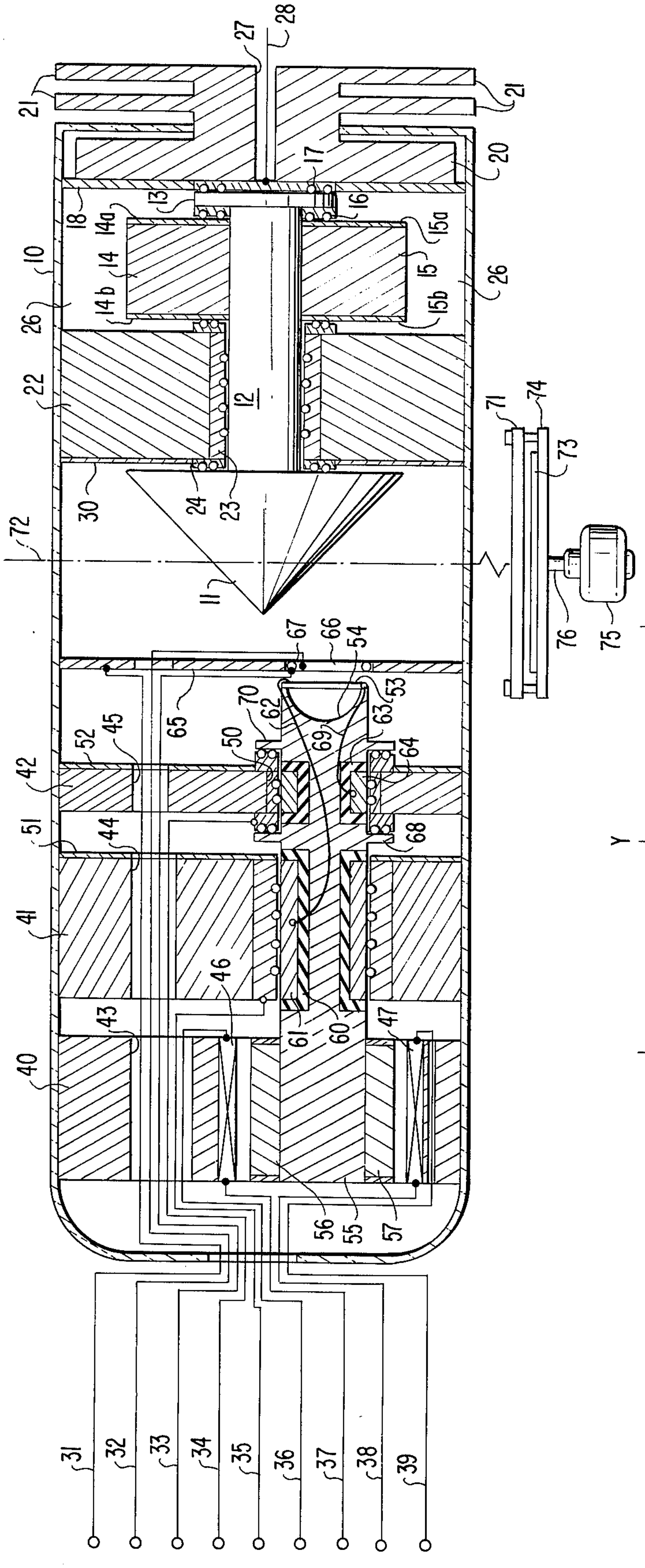
FIG. 1 is a side, partially sectional view of an exemplary X-ray apparatus including an X-ray tube according to the present invention, parts of the tube being shown in cross-section.

As illustrated in FIG. 1, an illustrative embodiment of an X-ray apparatus according to the present invention is constituted by an X-ray tube having an assembly mounted within a glass envelope 10. The assembly includes a conically shaped anode 11 positioned on the end of a shaft 12. The other end of the shaft 12 is provided with an outwardly extending flange 13. Two magnets 14 and 15 are fixed to the shaft 12 in the vicinity of the flange 13. A first ball bearing collar 16 is positioned between each of the magnets 14 and 15 and the flange 13 of the shaft 12, ball bearings within the collar 16 being in contact with respective bearing surfaces **14*a* and 15*a* on the magnets 14 and 15. A second ball bearing collar 17 carried by a metallic support 18 is positioned against the rearward portion of the flange 13 of the shaft 12. A heat sink 20, having a plurality of cooling fins 21 positioned externally of the envelope 10**, extends through the envelope 10 in contact with the metallic support 18 so as to provide a path for conducting heat from the anode 11, via the shaft 12 and the support 18, to the outside of the envelope 10.

A ring-shaped support 22 is fixed to the inner surface of the envelope 10 and carries about its inner periphery a ball bearing collar 23 within which the shaft 12 is positioned. The ball bearing collar 23 is provided on each of its ends with respective upstanding collar extensions 24 and 25. The extension 24 contains ball bearings which contact the rearward flat face of the anode 11, the upstanding part 25 contains ball bearings which contact respective bearing surfaces 14*b* and 15*b* provided on the magnets 14 and 15. A space 26 is provided radially outward from the anode shaft 12 and the magnets 14 and 15, windings (not shown) and associated leads may be positioned in the space 26 or outside of the envelope 10 for establishing a rotating magnetic filed, which, with the magnets 14 and 15 effect the rotation of the shaft 12 and the anode 11. In practice the frequency of the current applied to these windings is sufficient to result in a rotation of the anode 11 about its axis at several thousand r.p.m., a conventional feature of many X-ray tubes.

The heat sink 20 is provided with an aperture 27 which extends through the heat sink 20 so as to enable a lead 28 to be connected to the metallic support 18 so as to provide a means for supplying anode voltage to the anode 11, via the support 18, the collar 17 and the anode shaft 12. As illustrated, a conventional electromagnetic shield 30, made of a suitable conventional alloy is provided between the ring-shaped support 22 and the anode 11. This electromagnetic shield 30 may be, as illustrated, carried by the ring-shaped support 22. It is to be appreciated that in varients of the X-ray tube shown, the shield 30 need not be present.

The magnets 14 and 15, being permanently mounted to the shaft 12 of the anode 11, are forced to rotate about the longitudinal axis of the X-ray tube at several thousand r.p.m. by the application of a suitable alternating current of selected frequency to the windings which may be mounted either in the space 26 or on the outside of the tube 10. As a result the shaft 12 rotates about its axis and carries with it the anode 11, during operation.

The ball bearing collars 16, 17 and 23 prevent transverse and longitudinal drift of the rotating anode assembly constituted by the anode 11, the shaft 12, and the magnets 14, 15. The heat sink 20 dissipates heat produced in the anode 11 and generated by the de-acceleration of electrons.

As thus far described, the X-ray tube shown in FIG. 1 is of a conventional nature.

As shown to the left in FIG. 1, the illustrative embodiment of an X-ray apparatus includes a plurality of electrically conductive, insulated leads 31–39 which extend through the glass envelope 10. Three disc-shaped cylindrical support members 40–42 are fixedly positioned in spaced-apart relationship within the glass envelope 10 at differing distances from the anode 11. Each of the members 40–42 is provided with a respective aperture 43–45 each aperture being axially aligned with the other two of these apertures and offset from the axis of rotation of the conical anode 11. The apertures 43–45 decrease in diameter from one to the next of the members, the member 41 which is closest to that end of the glass envelope 10 through which the leads 31–39 extend is the largest of the three apertures. The purpose of the apertures 43–45 is to allow the leads 31–39 to be connected to parts within the X-ray tube.

Each of the cylindrical support members 40–42 is provided with a respective additional aperture (unnumbered), aligned with one another and offset from the axis of rotation of the conical anode 11 in a direction opposite to the offset of the apertures 43–45. The support member 40 has fixedly attached thereto and insulated therefrom respective induction coils 46 and 47, these induction coils being spaced substantially 180° apart from one another and facing the additional aperture in the member 40. A ball bearing collar 48 is positioned fixedly about the inner periphery of the cylindrical support member 41, its ball bearings facing inwardly toward the additional aperture in the member 41. The cylindrical support member 42 is similarly provided with a ball bearing collar 50 which is fixed to its inner periphery, its ball bearings extending inwardly toward the additional aperture in the member 42. As illustrated, the ball bearing collar 50 is provided with upstanding portions at each of its ends. The support members 41 and 42 are provided respectively on their faces which face toward the conical anode 11 with respective electromagnetic shields 51 and 52.

The cathode of the X-ray tube shown in FIG. 1 is constituted by a filament 53 which extends across a conventional cup 54 provided in one end of a metal stem member 55. The stem member 55 is positioned within and in alignment with the center axes of the additional apertures in the cylindrical support members 40–42. The filament 53 is positioned on that end of the stem 55 which faces the conically-shaped anode 11. Within the additional aperture in the support member 40, and in spaced relationship from the induction coils 46 and 47, are provided respective magnets 56 and 57 which are fixed to the stem 55 with their respective south and north poles positioned against the stem 55. The portion of the stem 55 within the additional aperture in the support member 41 is of somewhat lesser diameter than that portion which supports the magnets 56 and 57. This portion of the stem 55 of reduced diameter is provided with a circumferentially extending insulator 60 which carries a slip ring 61. The slip ring 61 is connected electrically to one end of the filament 53 via an insulated conductive lead 62. The slip ring 61 is arranged to contact the ball bearing collar 48 which is connected to the electrical lead 35 to supply voltage to one end of the filament 53.

That portion of the stem 55, which is positioned within the additional aperture in the support member 42, is provided with a second circumferentially extending insulator 63 which carries a slip ring 64. The slip ring 64 is connected to the other end of the filament 53 via an insulated electrically conductive lead 69. The slip ring 64 contacts the collar 50 which is electrically connected to the lead 34 which extends through the apertures 43 and 44.

An electrically grounded mask 65 provided with an aperture 66 adjacent to the filament 53 is positioned across the inside of the envelope 10. The mask 65 is connected electrically to the lead 31 which is to constitute a ground point for the apparatus. A focusing coil 67 is positioned about the aperture 66, this focusing coil 67 being electrically connected to the leads 32 and 33 which supply current to the focusing coil 67. Terminals of the induction coils 56 and 57 are connected respectively to the leads 36, 37 and 38, 39 which supply current of a selected frequency and phase to these coils to set up a rotating magnetic field. The frequency is selected to assure that the stem 55, by virtue of the action of the magnets 46 and 47 which are fixed thereto, rotates about its longitudinal axis at a velocity sufficient to cause the filament 53 to rotate about its center point at least several times during an exposure period. Exposure times in the range of from about 1/30 of a second to 1/10 of a second are not unknown in current practice. The frequency is desirably chosen to assure that the filament 53 is rotated at least ten times per exposure and more preferably one hundred times per exposure. It is to be understood, however, that fewer revolutions per exposure can achieve the aims of the present invention provided an integral number of revolutions, even one, takes place during exposure.

In operation thermionically emitted electrons from the filament 53, heated by an appropriate current supplied by voltage applied between the leads 34 and 35, are accelerated to the rotating anode 11 by an appropriate voltage applied between the lead 34 and the lead 28. Heating current from the lead 34 passes through the ball bearing collar 50 into the slip ring 64, through the filament 53 to the conducting slip ring 61 and to the lead 35, via the ball bearing collar 48. The magnets 56 and 57 are permanently attached to the filament stem 55.

Transverse drift of the rotating filament stem 55 is prevented by collar rings 68 and 70 which are, as shown, integral with the stem 55 and in contact with the ball bearing collar 50. The voltage applied to the focusing coil 67, via the leads 32 and 33, which in combination with the electrically conducting mask 65 grounded to the lead 31 may be used to shape the electron beam emitted by the filament 51. It is to be understood that the coil 67 and the mask 65 need not be present, but are desirable in many instances.

As shown in FIG. 1 an X-ray transparent support 71, adapted to hold or to support an object to be subjected to X-ray radiation, is positioned perpendicular to an axis 72 along which the central emergent X-ray beam of the X-ray field produced by the tube travels. An image receptor 73, which can be a conventional X-ray film, is positioned beneath the support 71 on a receptor holder, shown somewhat diagrammatically at 73.

The support 71 and the holder 73 are mechanically connected together so that these members may be rotated in synchronism by an electric motor 75 which is coupled to the holder 74 via a drive shaft 76. The object support 71 and the holder 74 need not be rotated by the motor 75 to achieve the aims of the invention when the filament 53 is rotated, as discussed above. In practice, the illustrated X-ray tube may be operated with the filament 53 stationary during exposure periods, the same effect being achieved by rotating the support 71, with the object to be subjected to the X-ray radiation positioned thereon in synchronism with the image receptor 73. In this case the motor 75 is operated at such a speed to assure that at least a whole number of complete revolutions of the object and receptor 73 in a plane perpendicular to the axis 72 takes place during each exposure. As in rotating the filament 53, the number need not be whole if more than ten or more, for example, revolutions are achieved during a single exposure. In the event the motor 75 is used to provide for the relative rotation between the X-ray field and the receptor 73, any number of conventional X-ray tubes can be used in place of the tube shown in FIG. 1. Such arrangements constitute a second embodiment of the present invention.

A third embodiment of an X-ray apparatus according to the present invention is also contemplated. In this case, neither the object support 71 and the receptor 73 nor the filament 53 is rotated. Instead, an X-ray tube which may be of conventional internal construction is mounted for rotation by a drive means which rotates the tube about the axis along which the central emergent X-ray beam travels in a plane perpendicular to the axis of rotation, which corresponds to the axis 72 in FIG. 1. Voltages and currents can be supplied to the internal conventional electrodes and members of the tube via slip rings or the like. The drive means effects rotation of the tube so that at least one complete revolutions take place during each exposure, preferably several complete revolutions. In the event more than about ten revolutions are possible during an exposure, the revolutions need not be constituted by a whole number.

In order to investigate the radiographic effect of rotation of existing focal spot intensity distributions around the central axis of the distribution, experimental procedures have been carried out.

A conventional X-ray tube was positioned so that the central ray of the X-ray field was parallel to the axis of an optical bench. This procedure was accomplished by requiring the focal spot pinhold pictures obtained from an aperture mounted at a fixed height above the bench at the near and far positions of the optical bench to have a common center. The straight line determined by these two points then constitutes the central ray. A well regulated motor not unlike the motor 75 (FIG. 1) was then used to rotate an image receptor, corresponding to the image receptor 73 (FIG. 1) around this central ray keeping the central ray normal to the plane of the image receptor.

In this manner, using an integral number of revolutions one can obtain a pinhole picture of the central ray projection of a rotated focal spot intensity distribution. The unrotated and rotated focal spot intensity distributions, for the same exposure conditions, which result indicate that the rotated distribution is very different from the unrotated distribution and is much closer to an ideal type of Gaussian distribution.

One can note that rotation achieves a rotational symmetric Fourier transform, as it must, and in particular, the spurious transfer of certain frequencies has practically been eliminated. It should be noted, however, that this reduction in spurious resolution is accompanied by reduced high frequency transfer capability on one axis and an increased capability on the other axis. In this sense, rotation seems to produce an averaging of the $v_x$ and $v_y$ transfer capability, resolution being essentially the same in all radial directions.

Because the unrotated focal spot intensity distribution is not isoplanatic across the image receptor plane, the focal spot intensity distribution that results from rotation of the image plane will also not be isoplanatic. However, for positions close to the central ray and for large focal-image receptor plane distances, the focal spot intensity distributions can be assumed isoplanatic. An example of the type of radiographic image that would result by use of a rotated focal spot intensity distribution exposing a finite object was obtained by mounting the object in a plane parallel to the image receptor plane and having both planes driven synchronously by the same motor, which corresponds to the motor 75 (FIG. 1).

A similar procedure was followed in order to obtain radiographs illustrating the effect of the rotated intensity on the imaging of simulated small blood vessels. This procedure further illustrated the advantages of reducing the effect of spurious resolution on the images of the simulated blood vessels.

The asymmetrical nature of the unrotated focal spot intensity distribution can be seen from images which are dependent on the relative orientation of the simulated small diameter flood vessel and the focal spot. Vessels lying essentially parallel to the long axis of the focal spot distribution showed spurious (dual) imaging while those vessels horizontal to the long axis were imaged quite sharply and do not show spurious resolution. This strong directional dependence of image quality of fine vessels on the orientation of the vessel relative to the focal spot is a limiting factor to the utility of any single (average) number characterization of a non-symmetric focal spot. Images produced from rotated focal spot intensity distributions will not, of course, depend on the relative orientation of the vessel and focal spot. It should be pointed out, however, that although the image was essentially independent of orientation, the high frequency transfer of the spatial frequency spectrum of the blood vessel is a compromise between the two extremes obtained from the unrotated focal spot with the image oriented parallel and perpendicular to the focal spot. Thus, there are certain regions of the image obtained from the rotated focal spot which appear to have less edge (high frequency) definition than the image obtained from the unrotated focal spot.

A rotation of the image receptor achieves the image effect of a rotationally symmetric focal spot distribution at the plane of the image receptor. The technique of a synchronous rotation of the object and image receptor, according to one embodiment of the present invention has usefulness in some areas of practical radiology. It is of course desirable to obtain such a rotationally symmetric intensity distribution without the need of rotation of the object and image receptor in many instances. Considerations of symmetry indicate, in these instances, that a similar rotationally symmetric intensity distribution can be obtained by rotation of the filament or the X-ray tube itself, as the case may be, in accordance with two other embodiments of the present invention as set out above, distribution leaving the cathode would be rotationally symmetric.

In conclusion, it has been demonstrated that simple rotation techniques can produce rotationally symmetric focal spots with Gaussian-like intensity distributions. The differences in the radiographic image that results from a given (nonsymmetric) focal spot distribution compared to the image obtained from the same focal spot distribution subjected to uniform rotation are significant. The images produced from the rotationally symmetric distributions typically show: decreased spurious imaging, independence of image appearance on object-focal spot orientation, and some reduced edge-sharpness in certain directions.

Figure 2:
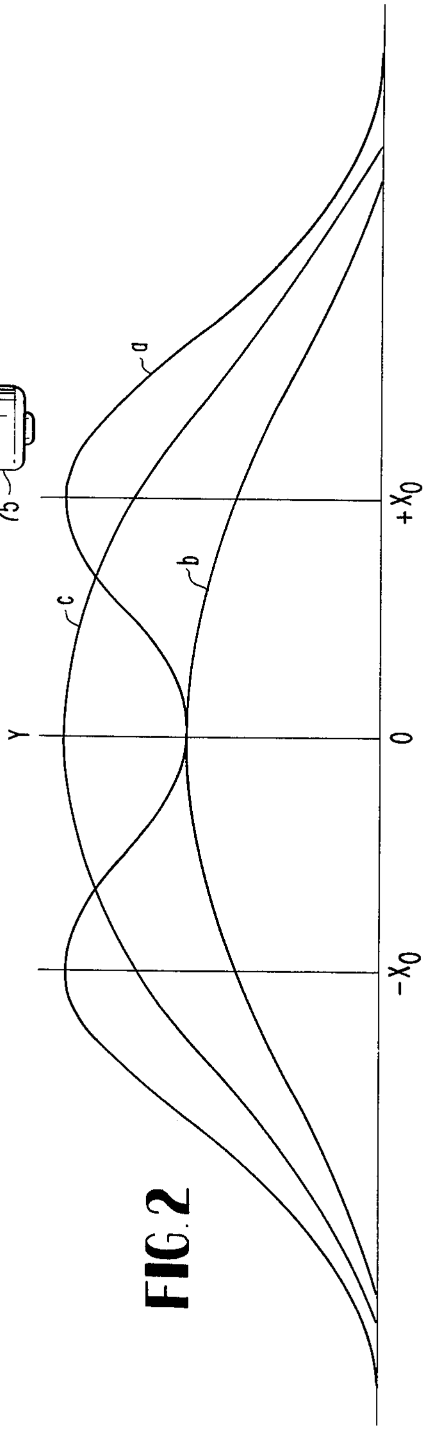
FIG. 2 is a graphical representation of focal spot intensity for a rotated and non-rotated focal spot which is useful in understanding the operation of the X-ray apparatus shown in FIG. 1.

Turning to FIG. 2, a cross-section through the x-axis of an unrotated and rotated intensity distribution of an X-ray field for a conventional unrotated field is illustrated by curve *a* which shows two peaks at $-X_O$ and $+X_O$. If the filament or X-ray tube itself or the image receptor is rotated, in accordance with the present invention the distribution becomes of the Gaussian type, a bell-shaped curve *b* results. This curved can be normalized, as indicated by curve *c*, for comparison purposes. As can be seen, the intensity distribution of appratus according to the present invention differs considerably from that of conventional apparatus.

It is to be appreciated that the foregoing description and accompanying illustrations have been set out by way of example, not by way of limitation. Other embodiments and numerous varients are possible within the spirit and scope of the present invention, its scope being defined by the appended claims.

What is claimed is:

1. An X-ray apparatus comprising an envelope, an anode, a cathode and means for providing a rotationally symmetric, Gaussian-like focal spot distribution, wherein said cathode is a filament having a central point and being positioned in a given plane, wherein said means for providing a rotationally symmetric, Gaussian-like focal spot distribution comprises means for rotating said filament in said given plane about said central point, and wherein said means for rotating effects an integral number of revolutions of said filament during an exposure interval.

2. An X-ray apparatus according to claim 1, wherein said means for rotating effects at least ten revolutions of said filament in said plane during an exposure interval.

3. An X-ray apparatus according to claim 1, wherein said means for rotating effects at least one complete revolution of said filament during an exposure interval.

4. An X-ray apparatus according to claim 1, wherein said filament is carried on a stem, said stem being rotatable within said envelope.

5. An X-ray apparatus according to claim 4, wherein said means for rotating include magnet means fixed to said stem and induction coil means fixedly positioned adjacent said magnet means.

6. An X-ray apparatus comprising an envelope, an anode, a cathode and means for providing a rotationally symmetric, Gaussian-like focal spot distribution, wherein said cathode is a filament having a central point and being positioned in a given plane, wherein said means for providing a rotationally symmetric, Gaussian-like focal spot distribution comprises means for rotating said filament in said given plane about said central point, and wherein said filament is carried on a stem, said stem being rotatable within said envelope.

7. An X-ray apparatus according to claim 6, wherein said means for rotating include magnet means fixed to said stem and induction coil means fixedly positioned adjacent said magnet means.

8. An X-ray apparatus according to claim 6, wherein said means for rotating effects at least ten revolutions of said filament in said plane during an exposure interval.

9. An X-ray apparatus according to claim 6, wherein said means for rotating effects at least one complete revolution of said filament during an exposure interval.

10. An X-ray apparatus according to claim 6, wherein said means for rotating effects an integral number of revolutions of said filament during an exposure interval.

11. An X-ray apparatus comprising:

an envelope;

an anode positioned within said envelope;

a cathode positioned within said envelope, said cathode being a filament having two ends to which filament current supplying connections are made and a central point midway between said ends, and being positioned in a given plane; and means for providing a rotationally symmetric, Gaussian-like focal spot distribution, said means including means for rotating said filament, relative to said envelope, in said given plane about said central point.

12. An X-ray apparatus according to claim 11, wherein said means for rotating effects at least ten revolutions of said filament in said plane during an exposure interval.

13. An X-ray apparatus according to claim 11, wherein said means for rotating effects at least one complete revolution of said filament during an exposure interval.

14. An X-ray apparatus according to claim 11, wherein said means for rotating effects an integral number of revolutions of said filament during an exposure interval.

15. An X-ray apparatus according to claim 11, wherein said means for providing a rotationally symmetric Gaussian-like distribution includes at least one focusing coil positioned in proximity to said filament.

16. An X-ray apparatus according to claim 11, wherein said filament is carried on a stem, said stem being rotatable within said envelope.

17. An X-ray apparatus according to claim 16, wherein said means for rotating include magnet means fixed to said stem and induction coil means fixedly positioned adjacent said magnet means.

18. An X-ray apparatus according to claim 11, wherein said means for providing a rotationally symmetric, Gaussian-like focal spot distribution includes a mask connected to a point of reference potential and provided with an aperture positioned with said aperture adjacent said filament.

19. An X-ray apparatus according to claim 18, wherein said means for providing a rotationally symmetric Gaussian-like distribution includes at least one focusing coil positioned about said aperture.

* * * * *